(12) United States Patent
Gwathmey

(10) Patent No.: US 6,960,560 B2
(45) Date of Patent: Nov. 1, 2005

(54) IRON CHELATOR DELIVERY SYSTEM

(75) Inventor: Judith K. Gwathmey, Cambridge, MA (US)

(73) Assignee: Gwathmey, Inc., Cambridge, MA (US)

( * ) Notice: Subject to any disclaimer, the term of this patent is extended or adjusted under 35 U.S.C. 154(b) by 0 days.

(21) Appl. No.: 09/751,769

(22) Filed: Dec. 29, 2000

(65) Prior Publication Data

US 2001/0033860 A1 Oct. 25, 2001

Related U.S. Application Data

(60) Provisional application No. 60/173,924, filed on Dec. 30, 1999.

(51) Int. Cl.$^7$ .......................... A61K 9/127; A61K 31/16; A61K 38/00
(52) U.S. Cl. ..................... 514/2; 424/152.1; 424/172.1; 424/178.1; 424/450; 514/616
(58) Field of Search ........................... 424/152.1, 172.1, 424/178.1, 450; 514/616, 2; 436/529

(56) References Cited

U.S. PATENT DOCUMENTS

| | | | | |
|---|---|---|---|---|
| 4,920,016 A | * | 4/1990 | Allen et al. | 424/450 |
| 5,534,241 A | * | 7/1996 | Torchilin et al. | 424/9.321 |
| 5,585,112 A | * | 12/1996 | Unger et al. | 424/450 |
| 5,854,007 A | * | 12/1998 | Ritter et al. | 435/7.23 |

FOREIGN PATENT DOCUMENTS

| | | |
|---|---|---|
| EP | 0068314 A1 | 6/1982 |
| WO | WO 92/01068 A1 | 1/1992 |

OTHER PUBLICATIONS

Hopkins, S.J., et al., "Liposome–Entrapped Desferrioxamine." *Drugs of the Future*, vol. 4, No. 7, pp.: 500–506 (1979).
Klibanov, Alexander L. et al., "Trageting of macromolecular carriers and liposomes by antibodies to myosin heavy chain." *American Journal of Physiology*, vol. 261, No. 4, Suppl., pp.: 60–65 (1991).
Lau, E.H. et al., "Improvement of Iron removal from reticuloendothelial system by liposome encapsulation of N,N'–bis [2–hydroxy–benzyl]–ethylenediamine–N.N'–diacetic acid (HBED)." *Journal of Laboratory and Clinical Medicine*, vol. 101, No. 5, pp.: 806–816 (1983).
Lau, E.H. et al., "Liposome–encapsulated Desferrioxamine in Experimental Iron Overload." *British Journal of Haematology*, vol. 47, pp.: 505–518 (1981).
Postma, N.S. et al., "Absorption and biodistribution of $^{111}$indium–labelled desferrioxamine ($^{111}$In–DFO) after subcutaneous injection of $^{111}$In–DFO liposomes." *Journal of Controlled Release*, vol. 58, pp.: 51–60 (1999).
Rahman, Yueh–Erh et al., "Liposomes as Delivery System for Iron Chelators." *Dev Iron Chelators Clin. Use*, Proc. Symp., 2$^{nd}$, pp.: 211–225 (1981).
Rahman, Yueh–Erh et al., "Application of Liposomes to Metal Chelation Therapy." *Liposomes Immunobiol.*, Proc. Natl. Symp., pp.: 285–299 (1980).
Young, S.P. et al., "Liposome Entrapped Desferrioxamine and Iron Transporting Ionophores: a New Approach to Iron Chelation Therapy." *British Journal of Heamatology*, vol. 41, pp.: 357–363 (1979).
Torchillin et al., "Preservation of antimyosin antibody after covalent coupling to liposomes," Biochem. Biophys. Res. Commun. 89(4), 1114–1119, 1979.
Dufresne et al., "Targeting lymph nodes with liposomes bearing anti–HLA–DR Fab' fragments," Biochim. Biophys. Acta, 1421(2), 284–294, 1999.
Maruyama et al., "Lipid composition is important for highly efficient target binding and retention of immunoliposomes," Proc. Nat'l. Acad. Sci., USA, 87:5744–5748, 1990.
Maruyama et al., "Possibility of active targeting to tumor tissues with liposomes," Adv. Drug. Deliv. Rev., 40 (1–2), 89–102, 1999.
Vingerhoeds et al., "Immunoliposomes in Vivo," Immunomethods, 4(3), 259–272, 1994.
Leserman et al., "Targeting to cells of fluorescent liposomes covalently coupled with monoclonal antibody or protein A," Nature, 288:602–604, 1980.

* cited by examiner

*Primary Examiner*—David Saunders
(74) *Attorney, Agent, or Firm*—Lowrie, Lando & Anastasi, LLP

(57) ABSTRACT

An iron chelator delivery system is disclosed. The system comprises iron chelator and a lipid carrier, e.g., a liposome. Methods for preparing and administering the iron chelator delivery system are also provided.

7 Claims, 16 Drawing Sheets

| UV SPECTRUM DATA FOR DESFERRIOXAMINE ||
| WAVELENGTH (nm) | ABSORBANCE |
| --- | --- |
| 190 | 0.184 |
| 200 | 0.244 |
| 204 | 0.306 |
| 208 | 0.283 |
| 220 | 0.127 |
| 230 | 0.040 |
| 240 | 0.007 |
| 245 | 0.002 |

CALIBRATION CURVE FOR
DESFERRIOXAMINE IN METHANOL

| WORKING SOLUTION IN 10ml | CONCENTRATION IN mg/ml | ABSORBANCE @ 204nm |
|---|---|---|
| 0.010mg | 0.0010 | 0.020 |
| 0.025mg | 0.0025 | 0.092 |
| 0.050mg | 0.0050 | 0.182 |
| 0.075mg | 0.0075 | 0.239 |
| 0.100mg | 0.0100 | 0.318 |
| 0.150mg | 0.0150 | 0.536 |
| 0.200mg | 0.0200 | 0.704 |

Blood Chemistry Values Before and After Liposome Infusion (with and without Desferrioxamine) were not significantly different.

| | Before | 24 Hours After | 5 Days After Infusion |
|---|---|---|---|
| SGOT | 100 ± 10 | 102 ± 10 | 100 ± 10 |
| SGPT | 36 ± 2 | 36 ± 2 | 37 ± 2 |
| *AP | 97 ± 1 | 97 ± 1 | 97 ± 0.4 |
| BUN | 17 ± 0.4 | 17 ± 1 | 18 ± 2 |
| Iron (blood) | 205 ± 7 | 203 ± 3 | 205 ± 5 |
| Total CK | 2 ± 0 | 0 ± 0 | 0 ± 0 |

* AP = alkaline Phosphatase

Reported values before injection and after injection of Desferrioxamine-encapsulated liposomes.

Fig. 5

IRON CHELATOR DELIVERY SYSTEM

RELATED APPLICATIONS

This application claims priority to U.S. Patent Application Ser. No. 60/173,924, filed on Dec. 30, 1999, the contents of which are incorporated herein by reference.

BACKGROUND OF THE INVENTION

Iron-overload due to transfusion currently occurs with any patient who receives more than 30 or 40 transfusions over the course of his or her life. The excess iron can injure any organ in the body. The heart and liver are particularly susceptible to damage, and failure of one of these organs is often the cause of death in patients with transfusional iron-overload. Transfusion related iron-overload is a major cause of morbidity and mortality in patients with a variety of transfusion-dependent anemias, hereditary hematchromatosis, including thalassemia major (Cooley's anemia).

Transfusion associated iron-overload develops in conditions characterized by severe, life-threatening anemia where transfusions substantially prolong life expectancy (Cairo, M. (1990) Introduction. Am. J. Pediatr. Hematol. Onco. 12:1–3). The most notable causes of transfusional iron-overload are the thalassemias, mild aplastic anemia, and congenital anemia (McLaren G. M. W. et al. (1983) CRC Crit. Rev. Clin. Lab. Sci. 126:896–899). Children with sickle cell disease and children who are stroke prone with sickle cell disease who receive chronic transfusions for complications may also suffer from iron-overload (Pegelow, C. et al. (1997) J. Pediatr. 126:896–899; Adams, R., et al. (1988) NEJM 339:5–11).

Transfused red cells are engulfed and destroyed at the end of their life span by stationary reticuloendothelial cells in the liver (Kupfer cells) and the spleen. The iron from the hemoglobin is removed and stored as hemosiderin. The reticuloendothelial cells return some of this iron to the circulation coupled to transferrin, and the iron is redistributed to the cells of the body. No physiological mechanism of iron excretion exists. Therefore, after a number of transfusions, the level of iron in the body reaches a toxic level. At that point, chelation therapy is required. Iron that is stored in hemosiderin is innocuous. This iron is in equilibrium, however, with a very small pool of so-called "free iron" in the cell. This pool of iron is so small that its size has never been satisfactorily determined. Better termed "loosely-bound iron," this material catalyzes the formation of reactive oxygen species through Fenton chemistry. These reactive oxygen species are the agents of cell injury.

Iron-overload, whether due to chronic transfusions or hereditary hemochromotosis, has a plethora of side-effects (Bonkovsky, H. (1991) American Journal of Medical Science 301:32–43), (Koren, A. et al. (1987) Am. J. Dis. Child. 141:93–96). Liver damage and heart failure are the two most common causes of death. Liver iron deposition initiates hepatic fibrosis, cirrhosis and death (Bonkovsky, H. (1991) American Journal of Medical Science 301:32–43). Congestive heart failure or death from cardiac arrhythmias is common (Koren, A. et al. (1987) Am. J. Dis. Child. 141:93–96). For disorders such as thalassemia major (by definition, transfusion-dependent thalassemia), iron-overload now is the limiting factor in survival. The advent of chronic transfusion therapy in the 1960's increased life span to the early to mid-twenties, however, the pernicious consequences of iron-overload were invariably fatal (Cooley, T. (1945) Am. J. Med. 209:561–572), (Piomelli, S. (1991) Hematol. Oncol. Clin. North. Am. 5:557–569).

Iron is one of the leading causes of pediatric poisoning deaths in the United States (Litovitz, T. L. et al. (1992) Am. J. Emerg. Med. 10:452–505). Numerous reports of serious or fatal poisonings have been cited in the medical literature (Litovitz, T. L. et al. (1992); Westlin, W. F. (1966) Clin. Pediatr. 5:531–535; Henriksson, P. et al. (1979) Scand. J. Haematol. 22:235–240) including five toddler deaths in Los Angeles county during a seven month period in 1992 (Weiss, B. et al. (1993) Morb. Mortal. Wkly. Rep. 42:111–113). It is clear that iron can cause serious morbidity and mortality, yet many clinicians and families remain unaware of the dangers of iron (Anderson, B. D. (Apr. 18, 2000) Medscape Pharamcists). Although uncommon, iron solutions may be absorbed through damaged or burned skin. Following ingestion of large amounts of iron, peak serum levels generally occur within 2 to 6 hours. After ingestion, iron in the +2 state is oxidized to the +3 state and attached to the transport protein, ferritin. The iron is then released from the ferritin to transferrin in the plasma, transported to the blood forming storage sites, and incorporated into enzymes in the body. Iron is eliminated slowly from the body. Even in states of iron overload, children may lose up to 2 mg per day. Ingestion of less than 20 mg/kg elemental iron is likely to produce GI symptoms. For patients who ingest greater than 60 mg/kg elemental iron, potentially life threatening symptoms may occur.

Furthermore, the emergence of drug resistant parasites, e.g., malaria, has intensified the search for new therapeutic approaches (e.g. drug combinations). One new approach under investigation is the administration of iron chelating agents (Cabantchik, Z. I. et al. (1996)Acta Haematol. 95:70–77; Van Zyl, R. L. et al. (1992) J. Antimicrob. Chemother. 30:273–278).

Patients with transfusion iron-overload, iron poisoning, and drug resistant parasitic diseases (e.g., malaria) are commonly treated with low molecular weight iron chelators. These compounds remove the excess, toxic iron from the patient's blood. The most commonly used drug worldwide is Desferrioxamine (Desferal®, Novartis). Therapy with Desferrioxamine is effective, but under-utilized because of drug delivery problems. Oral absorption of Desferrioxamine is very low. In some cases, Desferrioxamine infusion has proven not to be adequate (Westlin, W. (1996) Clin. Ped.5:531–535; Tenenbein, M. et al. (1992) Lancet 339:699–701; Adamson, I. Y. et al. (1993) Toxicol. Appl. Pharmacol. 120:13–19). In addition, the low molecular weight of this hydrophilic molecule (657 Da) leads to renal clearance in about 15 to 20 minutes. Consequently, the drug is given by continuous infusion over 12 to 16 hours. This is done either by subcutaneous infusion or by infusion into a permanent catheter. Such a long infusion duration is inconvenient and prone to infections and thrombosis. Desferrioxamine also has severe drawbacks in the treatment of parasitic diseases; (1) it is hydrophilic and poorly absorbed after oral administration; and (2) it is cleared rapidly after intravenous administration and iron chelators like Desferrioxamine do not readily penetrate into advanced growth stages of parasitized cells (Loyevsky, M. et al. (1993) J. Clin. Invest. 91:218–224). As a consequence, continuous infusion of iron chelators like Desferrioxamine over a three day period is required to obtain enhanced parasite clearance in human malaria (Mabeza, G. F. et al. (1996) Acta Haematol. 95:78–86). Nonetheless, many patients use Desferrioxamine suboptimally or not at all.

No other chelator has proven clinical efficacy. Searches for clinically effective alternatives to Desferrioxamine for transfusional iron-overload have thus far been futile. Some chelating agents, such as diethyltriamine pentaacetic acid (DPTA) are effective, but too toxic for clinical use. Other chelators (e.g., EDTA) bind other cations in addition to iron, making them unacceptable as treatment of transfusional iron-overload or iron poisoning.

One approach to the problem has been to immobilize Desferrioxamine to a large molecular matrix, thereby extending its biological half life. Immobilized Desferrioxamine depends on a shift in "pseudoequilibrium" conditions to produce a net outflux of iron from cells. The vast amount of storage iron exists inside cells, however, effectively out of the reach of immobilized Desferrioxamine. The problem is that the storage iron inside the cells remains a dangerous source of free radicals until it is chelated and inactivated by the Desferrioxamine in the matrix.

The only chelator currently in extensive clinical trial is Deferipone (L1). Deferipone removes excess iron reasonably well although it falls short of Desferrioxamine in this regard (Collins, A. et al. (1994) Blood 83:2329–33). The great appeal of Deferipone over Desferrioxamine is its oral absorption. For many patients, the convenience of an orally active chelator might more than compensate for lesser efficacy.

A number of clinical problems cloud Deferipone's future. Severe agranucloytosis occurs in about 2% of patients (al-Refaie, F. et al. (1992) Blood 80:593–9). Other significant side-effects of Deferipone include arthralgias and severe nausea (al-Refaie, F. et al. (1995) Br. J. Haematol. 91:224–229). Because of these and other problems, Deferipone's clinical future is far from assured. Therefore, there exists a need for an improved iron chelator delivery system.

SUMMARY OF THE INVENTION

The invention features an iron chelator delivery system comprising an iron chelator and a lipid carrier. The term "lipid carrier," as used herein, includes a carrier comprising lipid molecules, e.g., a liposome. The iron chelator and the lipid carrier of the iron chelator delivery system of the present invention can be combined in various ways. For example, the iron chelator can be coated with the lipids of the lipid carrier, e.g., iron chelators associated or attached to the surface of the lamellae of a lipid molecule or a liposome. Alternatively, the iron chelator can be encapsulated within the lipid carrier, e.g., iron chelators encapsulated within the central cavity of a liposome, intercalated within the lamellae of a liposome, or located between lamellae of the liposome.

Advantages of the iron chelator delivery system of the present application include: (1) a reduced toxicity based on the administration of a lower dose for a shorter period of time; (2) targeted delivery of the iron chelator without high renal clearance; (3) elimination of the pain associated with subcutaneous injections; (4) an increase in the half life of the iron chelator via targeted delivery of the drug to the heart and the liver, thus, reducing the amount of drug needed; and (5) entrapment of the drug in the liver up to 5 days, thus, allowing a longer period of time for iron chelation. Some iron chelation from the liver parenchyma will redistribute to other tissues and bind free iron.

Iron chelators within the scope of the present invention include, for example, Desferrioxamine, Deferipone, PIH (pyridoxal isonicotinoyl hydrazone and analogues), Rhodotorulic acid, HBED (N,N'-Bis(2-hydroxybenzyl) ethylenediamine-N,N-diacetic acid), HBPD (N,N'-Bis(2-hydroxybenzyl)propylene-1,3-diamine-N,N-diacetic acid), 2,3-dihydroxybebzoic acid, DTPA [diethyltriamine pentaacetic acid] and iron chelators produced by bacterial siderophores. Lipid carriers within the scope of the present invention include, for example, liposomes, e.g., multilamellar and unilamellar liposomes, as well as, phospholipid and nonphospholipid liposomes.

In one embodiment, the concentration of the iron chelator within the iron chelator delivery system is approximately 1 $\mu$M to 100 mM. In another embodiment, the size of the liposome is approximately less than about 10 nanometers to about 10 microns. In a preferred embodiment, the iron chelator delivery system is targeted for delivery to the heart and liver. For example, the lipid carrier can comprise cationic or anionic charge groups or antibodies specific for cardiac proteins, e.g., myosin, troponin, or myosin light chain proteins, vasculature proteins, endothelial cells, or matrix proteins. In another preferred embodiment, the lipid carrier is galactosylated or mannosylated. In another preferred delivery system the iron chelator delivery system is tagged with a label e.g. a radiolabel, which can be used for diagnostic imaging or identification of delivery to a particular site.

The present invention is also drawn to methods for preparing iron chelator delivery systems. Such methods comprise the steps of combining a lipid carrier or liposome with an iron chelator, and extracting the iron chelator-encapsulated liposomes to form an iron chelator delivery system.

Methods for treating iron-overload in a mammal, comprising administering to the mammal an iron chelator delivery system, e.g., an iron chelator associated with a lipid carrier, e.g., a liposome, are also provided. In a preferred embodiment, the iron chelator delivery system is administered so as to target specific organs, for example, the heart or the liver. Prior to administration, the iron chelator drug delivery system can be dissolved in a pharmaceutically acceptable excipient or carrier, e.g., saline, or water.

BRIEF DESCRIPTION OF THE DRAWINGS

FIG. 5 shows the blood chemistry values of normal animals before and after liposome infusion with and without Desferrioxamine.

DETAILED DESCRIPTION OF THE INVENTION

Figures 1, 2:
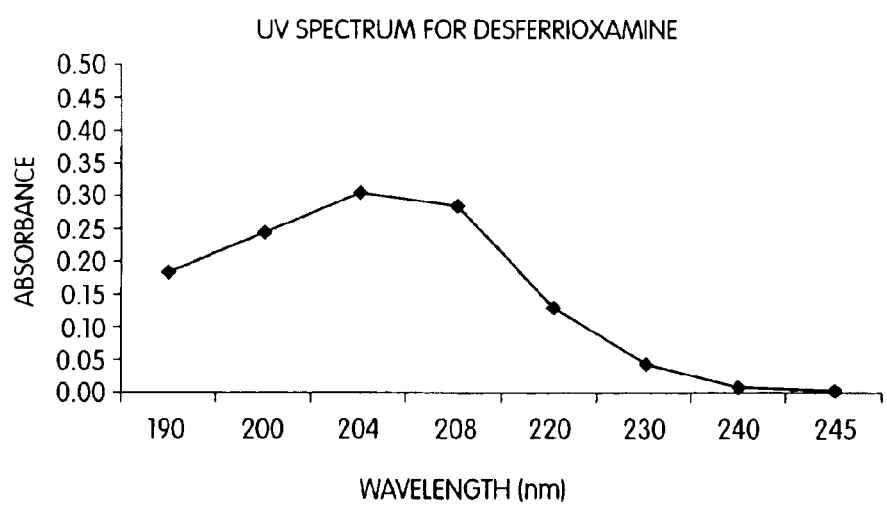
FIGS. 1 and 2 show the UV spectrum data for Desferrioxamine.

The present invention provides an iron chelator delivery system comprising an iron chelator and a lipid carrier. Iron chelators are compounds that remove the excess, toxic iron from the patient's blood, tissues and organs and include, for example, Desferrioxamine, Deferipone, PIH (pyridoxal isonicotinoyl hydrazone), Rhodotorulic acid, HBED (N,N'-Bis(2-hydroxybenzyl)ethylenediamine-N,N-diacetic acid), HBPD (N,N'-Bis(2-hydroxybenzyl)propylene-1,3-diamine-N,N-diacetic acid), 2,3-dihydroxybebzoic acid, DTPA [diethyltriamine pentaacetic acid], and iron chelators produced by bacterial siderophores. The term "lipid carrier," as used herein, includes a carrier comprising lipid molecules, e.g., liposomes. Liposomes are spherical structures made of materials having a high lipid content, e.g., surfactants or phospholipids. The lipids of spherical vesicles are organized in the form of lipid bilayers. The lipid bilayers encapsulate an aqueous or oil-filled volume which is either interspersed between multiple onion-like shells of lipid bilayers (forming multilamellar lipid vesicles) or the aqueous volume is contained within an amorphous central cavity. The most commonly known lipid vesicles having an amorphous central cavity filled with aqueous medium are the unilamellar lipid vesicles.

The present invention provides delivery systems for iron chelators. A hydrophilic drug, for example, Desferrioxamine, can be combined with a lipid carrier. The iron chelator can be coated with the lipids of the lipid carrier, e.g., iron chelators associated, intercalated, or attached to the surface of lipid molecules or to the lamellae of a liposome. Alternatively, the iron chelator can be encapsulated within the lipid carrier, e.g., iron chelators encapsulated within the central cavity of a liposome, intercalated within the lamellae of a liposome, or located between lamellae of the liposome. Other examples of lipid carrier formulations for the present iron chelator delivery system include, for example, the following: systems used with amphotericin B, which involve complexing the active ingredient with phospholipids as used in the formulation for ABELCET® (The Liposome Company, Inc., Princeton N.J.); cholesteryl sulfate complexes for injection similar to the formulation used for AMPHOTEC® (Sequus Pharmaceuticals, Menlo Park, Calif.) which comprises a sterile, pyrogen-free, lyophilized powder for reconstitution and intravenous administration, e.g., a formulation comprising a complex of Desferrioxamine and cholesteryl sulfate (upon reconstitution a colloidal dispersion of microscopic disc-shaped particles result); and a single bilayer liposomal drug delivery system such as used with AmBisome® (Nexstar Pharmaceuticals, Boulder Colorado (taken over by Gilead Sciences Foster City, Calif.)), wherein single bilayer liposomes are used. The drug becomes active when the lipid carrier, e.g., the liposome, fuses with cells to release its content.

There are many advantages for using the iron chelator delivery system of the present invention. The kidneys rapidly excrete small, hydrophilic iron chelator molecules, for example, Desferrioxamine. The iron chelator delivery system of the present invention, e.g., iron chelators associated with lipid carriers, e.g., liposomes, would not be filtered by the renal glomerulus. Even small unilamellar liposomes are about 10 nm in diameter, well above the filtration limit of the glomerulus. Therefore, the biological half-life of the iron chelator is extended when encapsulated within a liposome or associated with a lipid carrier.

Lipid carriers such as liposomes have been used for drug delivery for years with only limited success. A major problem has been targeting the liposomes to the proper organ or tissue. Attempts have been made to target chemotherapeutic agents which are encapsulated in liposomes to tumor cells, using a guidance system such as a tumor-specific antibody fragment embedded in the lipid bilayer. A problem associated with this technique is that many, if not most of the liposomes, are trapped by the liver and engulfed by the Kupfer cells in this organ. However, the liver is the major target organ in iron-overload, being the body's primary iron storage site. Therefore, reticuloendothelial (RE) cells engulf the iron chelator delivery system of the present invention, placing them in a position to intercept iron as it is released from degraded erythrocytes. Further, cardiac failure as a result of iron-overload is of great clinical importance. The heart can be targeted for delivery of Applicant's iron chelator delivery system, for example, Desferrioxamine combined with a lipid carrier by placing a cationic or anionic charge on the lipid carrier or by attaching antibodies specific to cardiac, vascular, endothelial, and matrix proteins to the lipid carrier. Also, the lipid carrier can be tagged with cardiac, liver, or tissue imaging labels. Cardiac proteins useful for targeting the heart include, for example, cardiac specific proteins such as myosin, troponin, and light chain myosin. Antibodies specific to endothelial, vascular smooth muscle cells, and matrix proteins can also be attached to the lipid carrier of the present iron chelator delivery system. In addition, selected delivery routes and an increase in the half life of the liposomes can enhance delivery to the heart.

Mammals, e.g., humans or animals, with transfusional iron-overload receive blood on a three to six week schedule, depending on the severity of their anemia. With the iron chelator delivery system of the present invention, the iron chelator delivery system, for example, Desferrioxamine combined with a lipid carrier, e.g., a liposome, would be infused at the end of the transfusion session and infused periodically. This would allow significant improvement over the current daily use of an infusion pump for 12–16 hours intervals. For example, thirty grams of Desferrioxamine encapsulated by liposomes would supply enough chelator for a month. This approach would be simpler than any available to date, including oral deferipone. Prior to administrations, the iron chelator delivery system can be dissolved in a pharmaceutically acceptable carrier. As used herein "pharmaceutically acceptable carrier" includes any and all excipients, solvents, dispersion media, coatings, antibacterial and antifungal agents, toxicity agents, buffering agents, absorption delaying or enhancing agents, surfactants, and micelle forming agents, lipids, liposomes, and liquid complex forming agents, stabilizing agents, and the like. The use of such media and agents for pharmaceutically active substance as known in the art. Except insofar as any conventional media or agent is incompatible with the active compound, use thereof in the therapeutic compositions is contemplated. Supplementary active compounds can also be incorporated into the compositions.

Conventional Desferrioxamine therapy costs currently between about $12,000 and $15,000 per year. Much of the expense involves the portable home infusion pumps, associated equipment (e.g., sterile infusion tubing and needles), and home nursing visits. These costs are eliminated by the current iron chelator delivery system. The iron chelator delivery system of the present invention can make iron chelation therapy available to underdeveloped countries that lack the financial resources needed for conventional Desferrioxamine chelation programs.

The iron chelator delivery system of the present invention eliminates the problems of local reactions associated with the subcutaneous administration of some iron chelators. For example, the chelator diethyltriamine pentaacetic acid (DTPA) was used to treat iron-overload early on, but caused severe local reactions that led to discontinuation of use. Intravenous administration, although more efficacious, is associated with the risk of infection, atrial thrombosis, and subclavical thrombosis. The indwelling catheter often curls into the atrium causing cardiac irritation and thrombosis. Right atrial thrombosis can lead to life threatening pulmonary embolism. The iron chelator delivery system as described herein would negate these problems.

The iron chelator delivery system of the present invention uses the chelator more efficiently. Compared to conventional therapy, lower amounts of chelator are required with Applicant's iron chelator delivery system which combines iron chelators with lipid carriers, e.g., liposomes. For example, by concentrating the iron chelator delivery system in the reticuloendothelial (RE) cells initially, the chelator has the greatest possible chance of intercepting iron. Therefore, lower dosages (and cost) of the drug are attained.

The lipid carriers of the present invention, e.g., liposomes, have a number of advantages over currently used options such as red cell ghosts as encapsulation agents. Liposomes are manufactured, while red cells ghosts are harvested. Therefore, supply is not an issue. Use of red cell ghosts entails some exposure, even slight, to biological pathogens. Finally, lipid carriers, e.g., liposomes, avoid alloimmunization issues because they lack red cell antigens (Rose, W. et al. (1990) Blood 76:1431–7).

This invention is further illustrated by the following examples which should not be construed as limiting. The contents of all references, patents and published patent applications cited throughout this application are hereby incorporated by reference.

EXAMPLE 1

Analysis of Iron-overloaded Animals Used in the Following Experiments

Eighty Hartley Guinea Pigs weighing 350–400 grams of both sexes were purchased. Iron dextran was administered at 1.5 g Fe/kg body weight intraperitoneal three times a week for four weeks. Animals were divided into groups to receive iron chelator without lipid carrier and chelator with lipid carrier as described herein. Desferrioxamine was given intramuscularly twice a day daily for a total concentration of 20 mg/kg daily for five days a week for four weeks. Intravenous lipid associated chelator was given intravenously three times a week at 0.6 mg.

Iron-overloaded animals were sacrificed and various organs were analyzed. The pattern of changes in the organs of all the iron-overloaded animals studied were similar with slight differences in severity. In the livers, there was a mild to moderate Kupffer cell hyperplasia in hepatic sinusoids. The Kupffer cells were distended with black globular material (Hematoxylin and Eosin) that was iron positive (Perl's iron stain). The Kupffer cells were clumped (granulomas) in those animals having moderate hyperplasia. The clumping was random and often associated with degeneration, necrosis, and replacement of hepatocytes. Rarely, lymphocytes were admixed. Hepatocytes also contained small amounts of iron positive material detected with special stains.

The hearts were characterized by cellular infiltration of macrophages containing iron. These cells were present in the epicardium and myocardium (perivascularly and in the interstitium) and in the adipose tissue at the base of the heart and perivascularly around the pulmonary vessels.

This model of iron overload therefore reflects the human condition and is suitable for testing the iron chelator delivery system described herein. Guinea pigs have been treated with the non-lipid associated chelator (8 mg/day 5 days per week) and the lipid-associated chelator (8 mg/day three days per week). In two animals, after only three injections of the lipid associated chelator, the color of the eyes and ears were restored to that seen in non-overloaded Guinea Pigs.

EXAMPLE 2

Preparation of an Iron Chelator Delivery System

Iron chelator delivery systems comprising an iron chelator and a lipid carrier, e.g., a liposome, can be prepared using the following standard procedures. General methods for preparing liposomes for use in the present iron chelator delivery systems are provided in Cortesi R., Esposito E., Gambarin S., Telloli P., Menegatti E., Nastruzzi C. (1999) "Preparation of liposomes by reverse-phase evaporation using alternative solvents," Journal of Microencapsulation 16(2):251–256; Buboltz J. T., Feigenson G. W., (1999) "A novel strategy for the preparation of liposomes: rapid solvent exchange," Biochimica et Biophysica Acta 1417(2):232–245; Bandyopadhyay P., Kren B. T., Ma X., Steer C. J., (1998) "Enhanced gene transfer into HuH-7 cells and primary rat hepatocytes using targeted liposomes and polyethylenimine," Biotechniques 25(2):282–284,286–292; Puu G., Gustafson I., (1997) "Planar lipid bilayers on solid supports from liposomes-factors of importance for kinetics and stability," Biochimica et Biophysica Acta 1327(2):149–161; Weiner A., (1994) "Liposomes for protein delivery: selecting manufacture and development processes," Immunomethods 4(3):201–209), the contents of which are incorporated herein by reference.

To determine the $\lambda_{max}$ value for Desferrioxamine, a solution of Desferrioxamine Mesylate in methanol is prepared and absorbence spectra determined using a Perkin Elmer Lambda 3B UV/VIS Spectrophotometer (FIGS. 1 and 2).

Figures 3, 4:
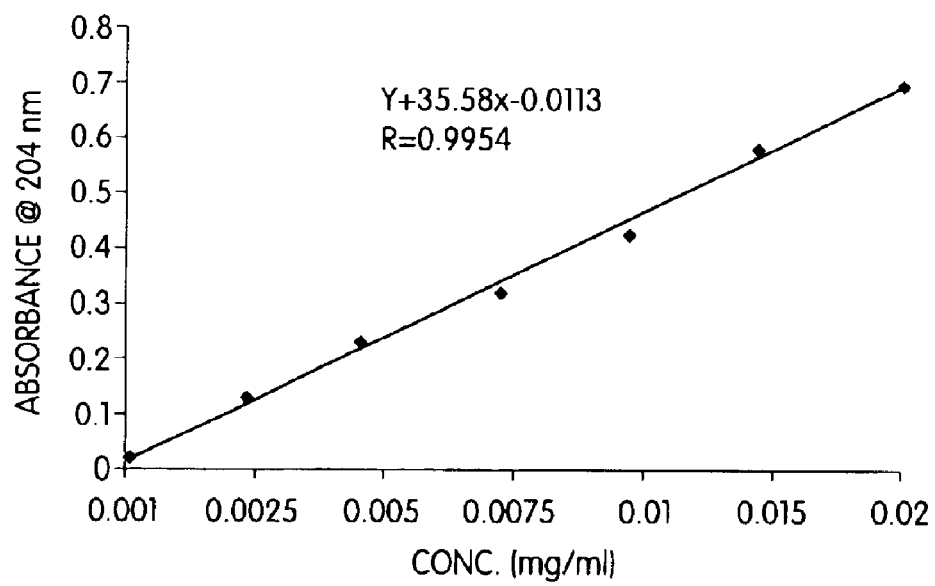
FIGS. 3 and 4 show the calibration curve for Desferrioxamine in methanol.
Figure 6:
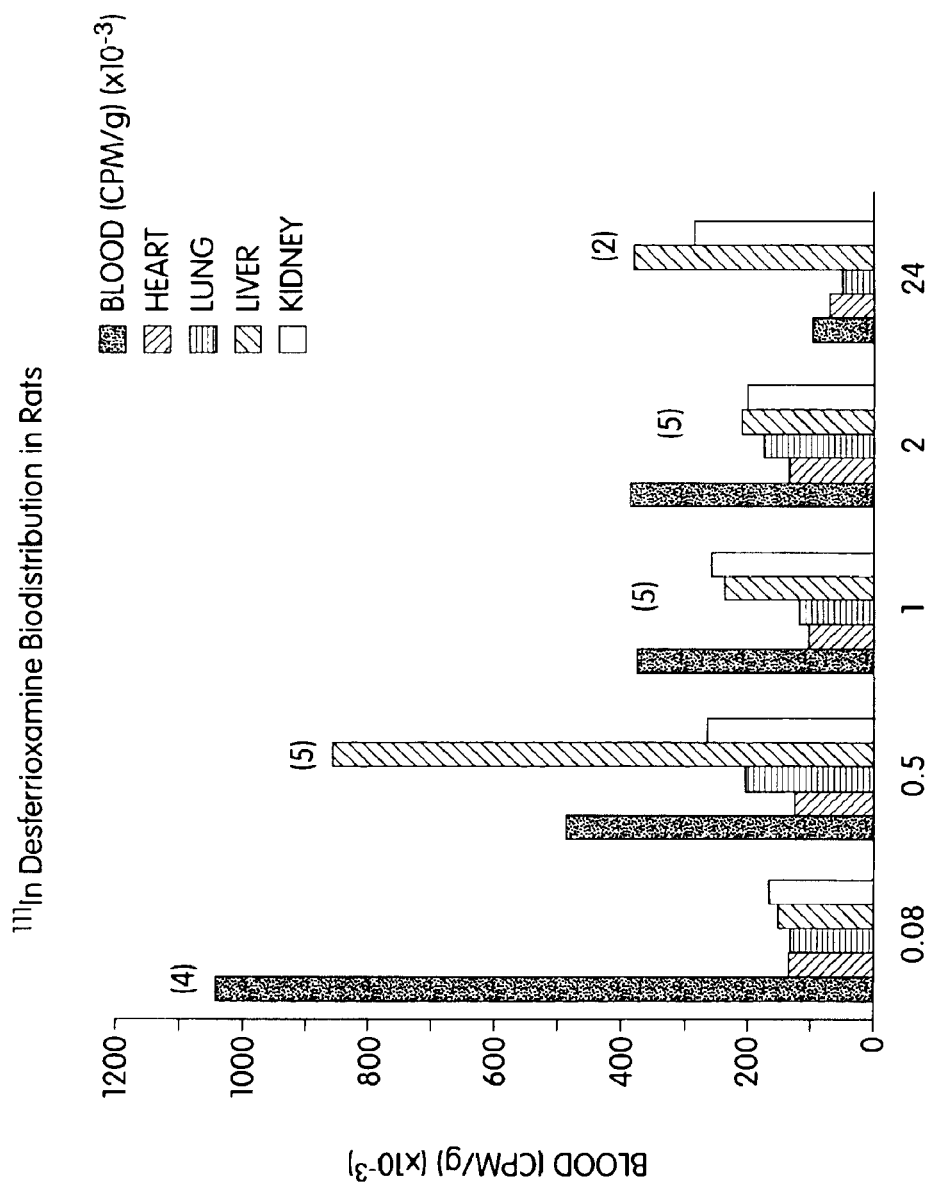
FIGS. 6–18 show $^{111}$In-Desferrioxamine biodistribution in rats.
Figure 7:
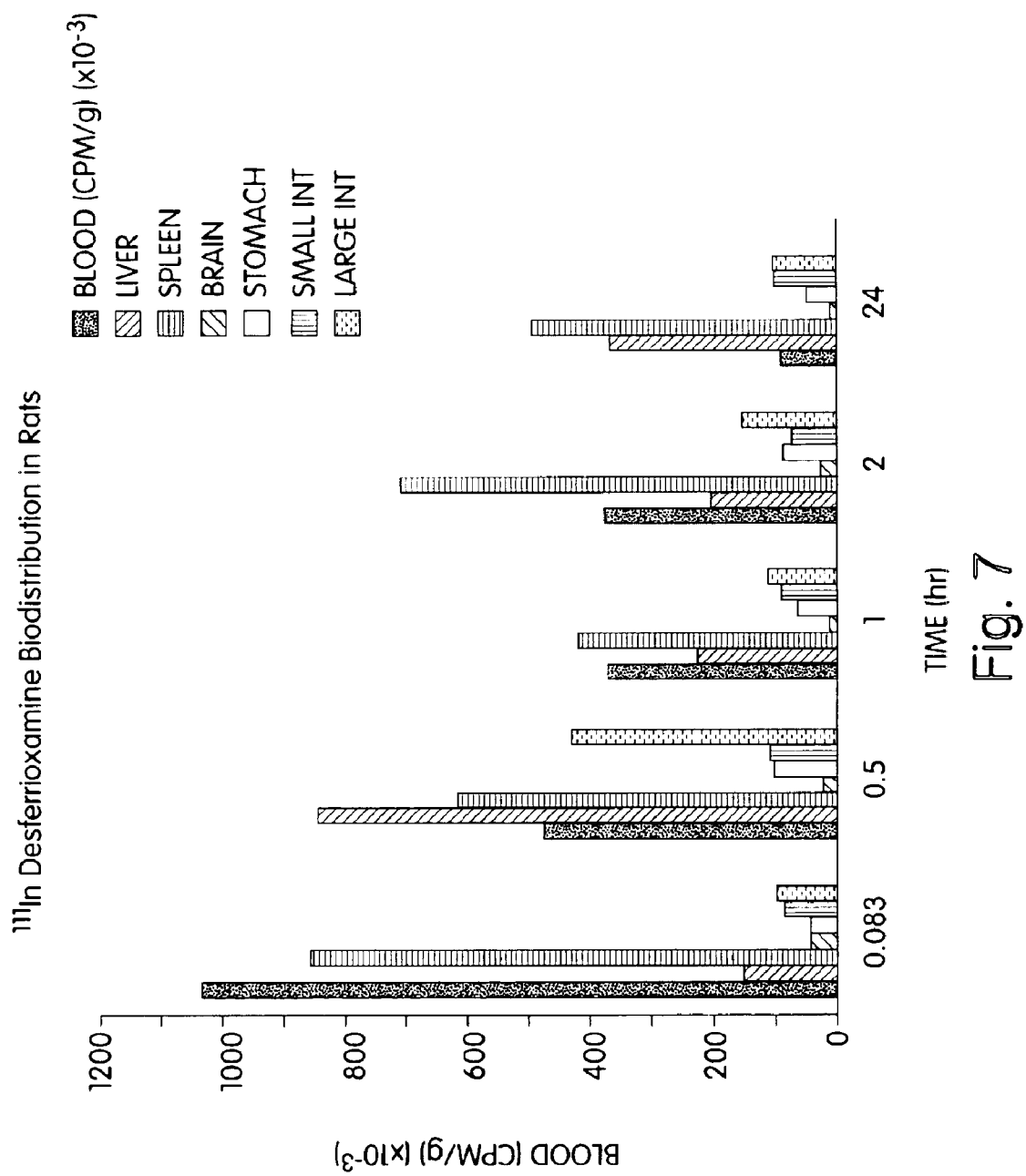
Figure 8:
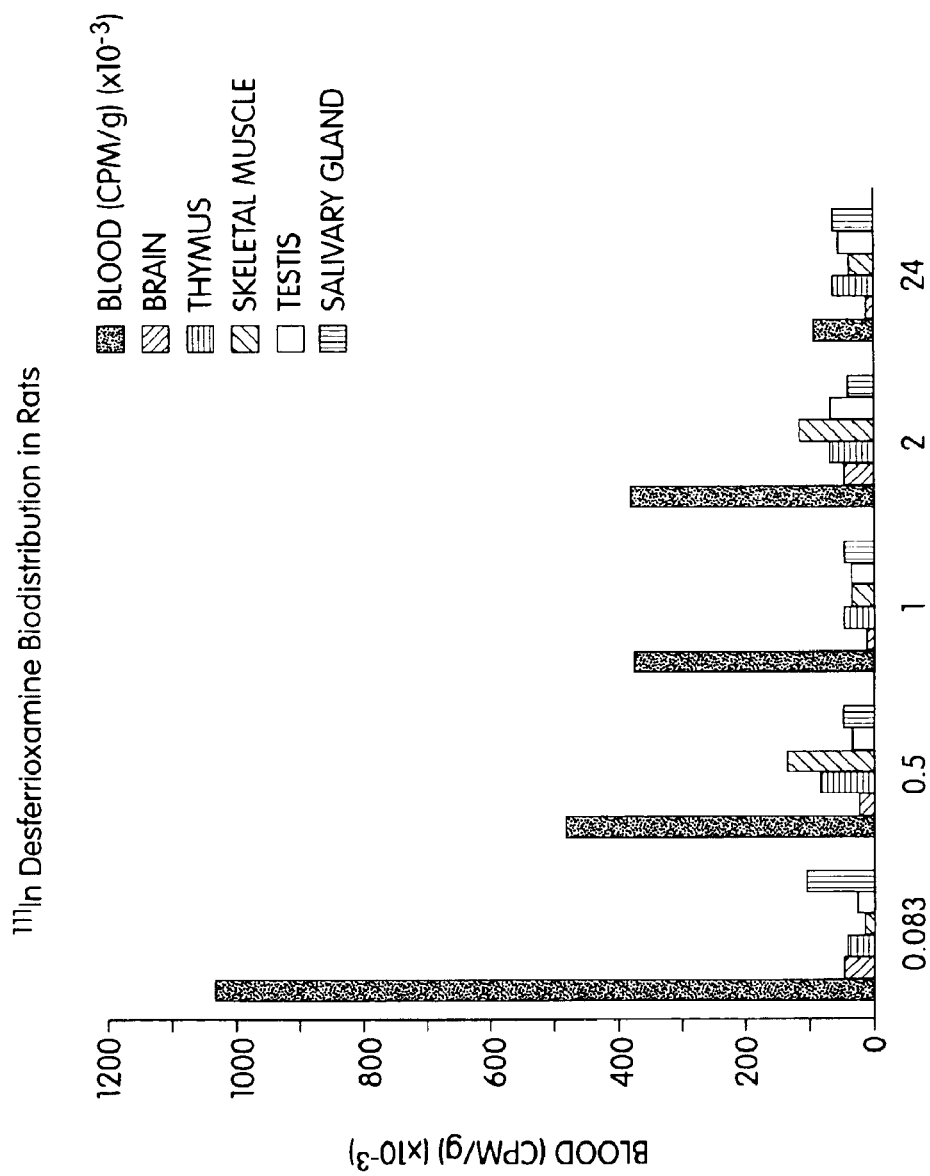
Figure 9:
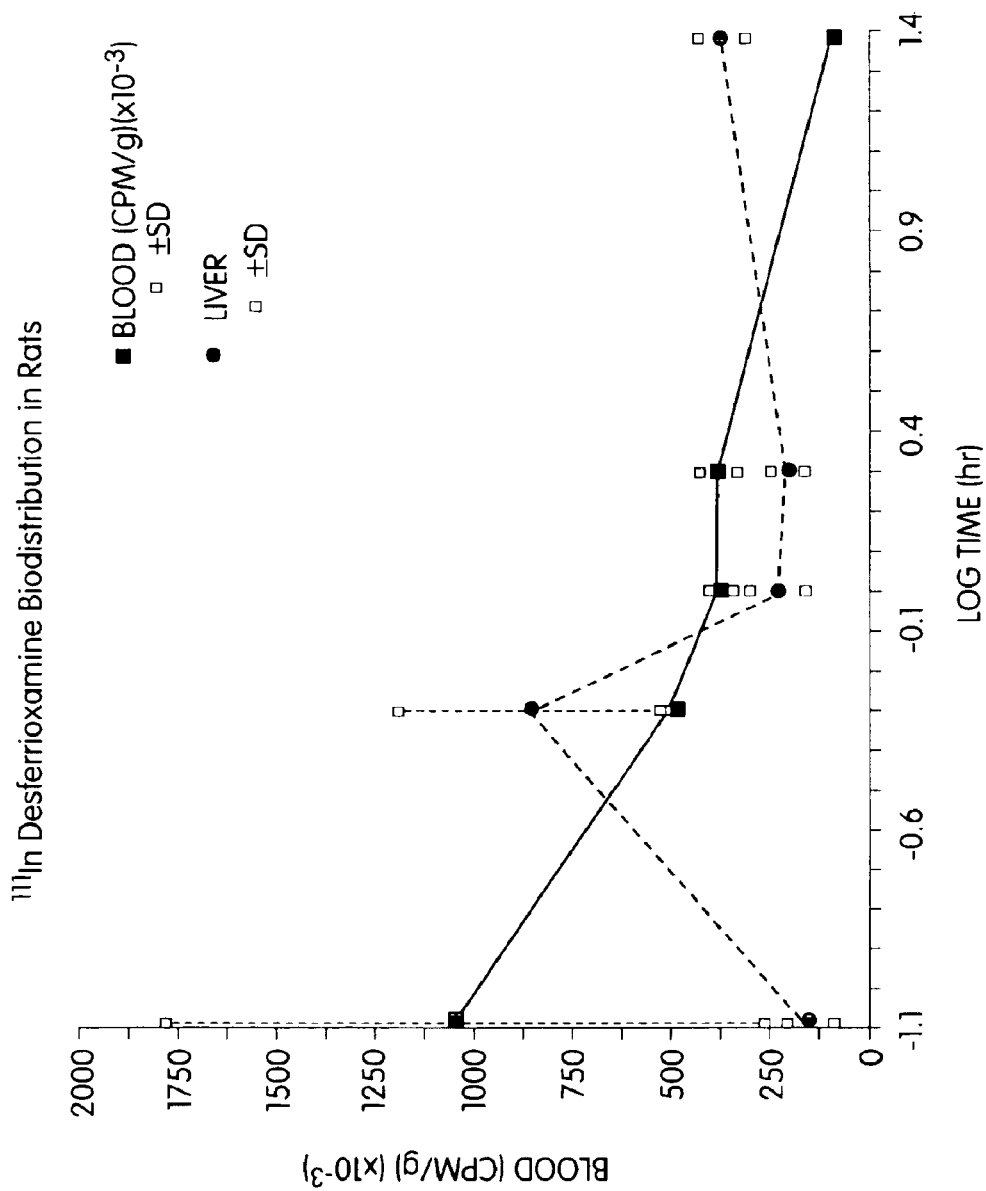
Figure 10:
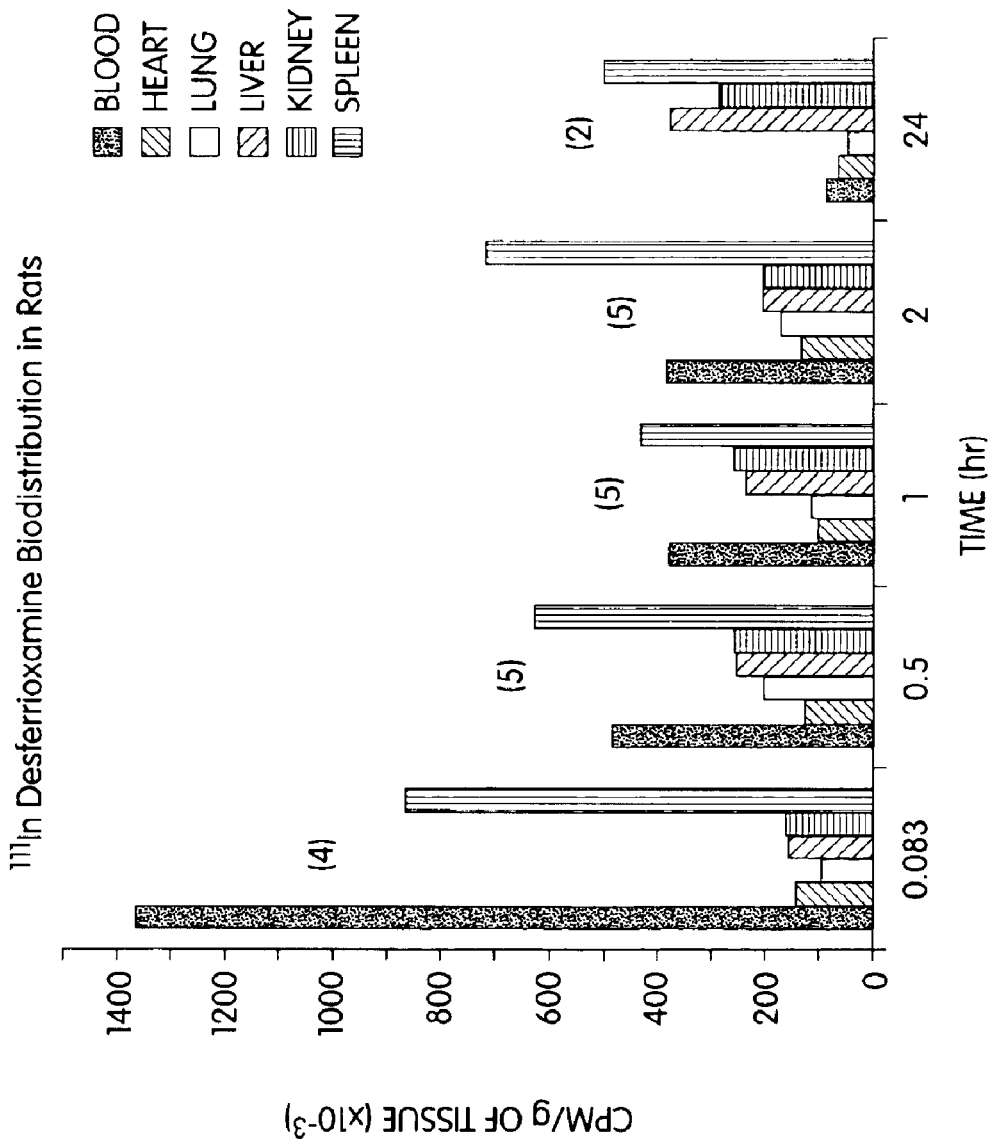
Figure 11:
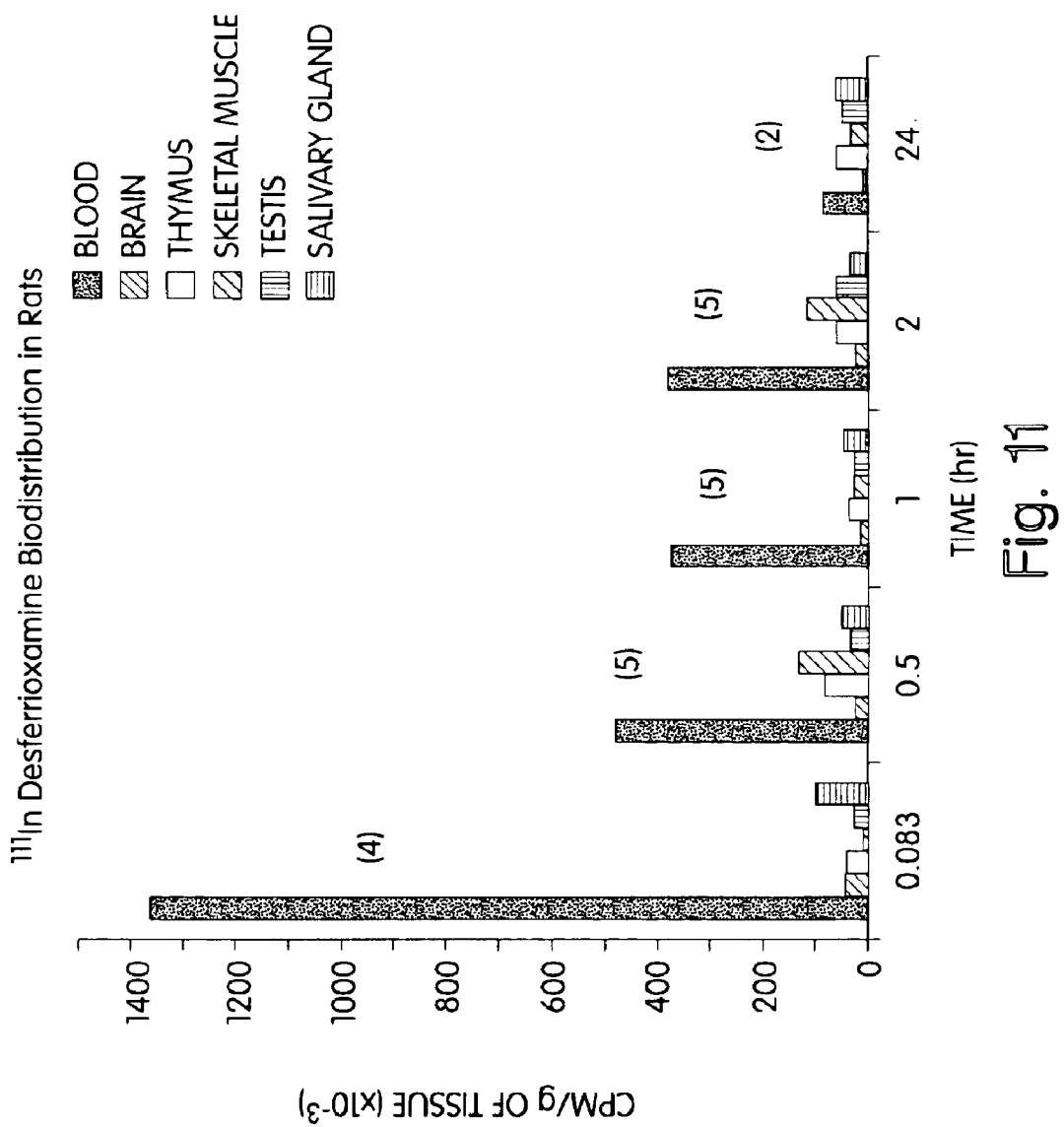
Figure 12:
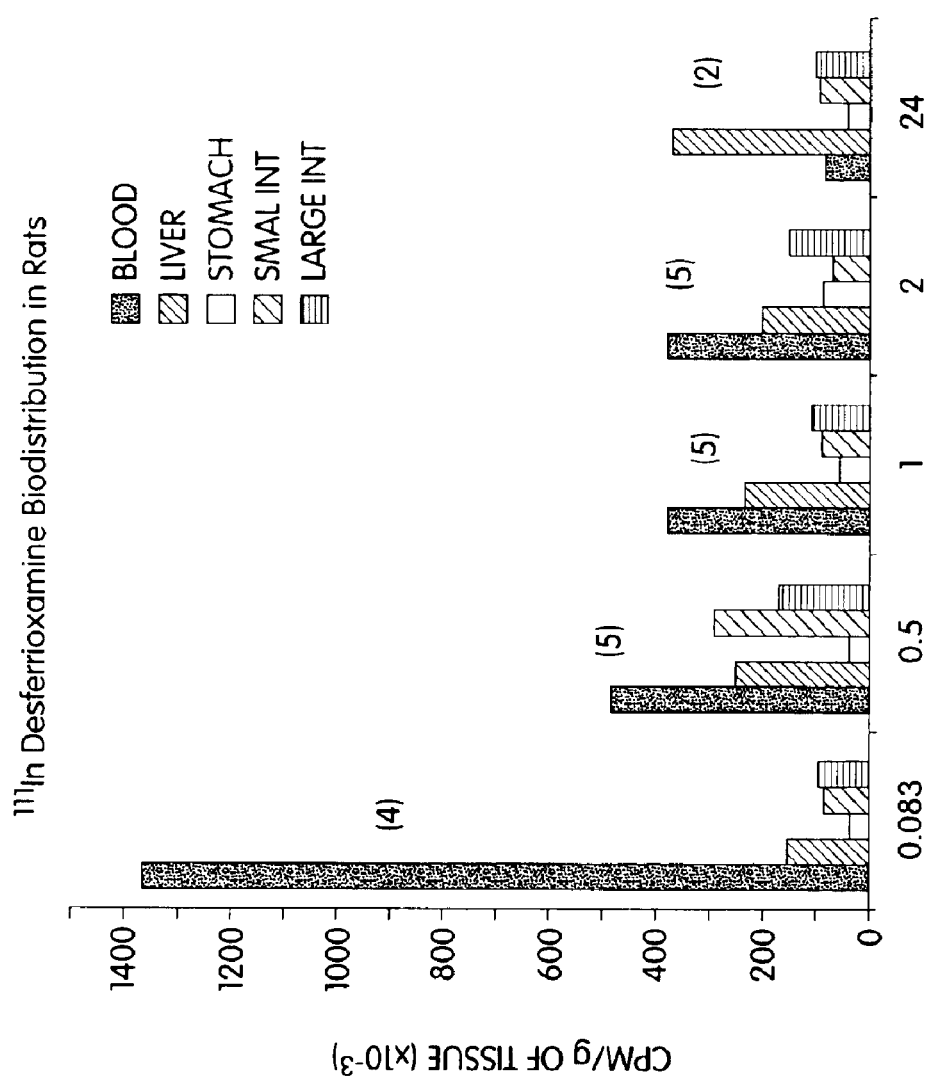
Figure 13:
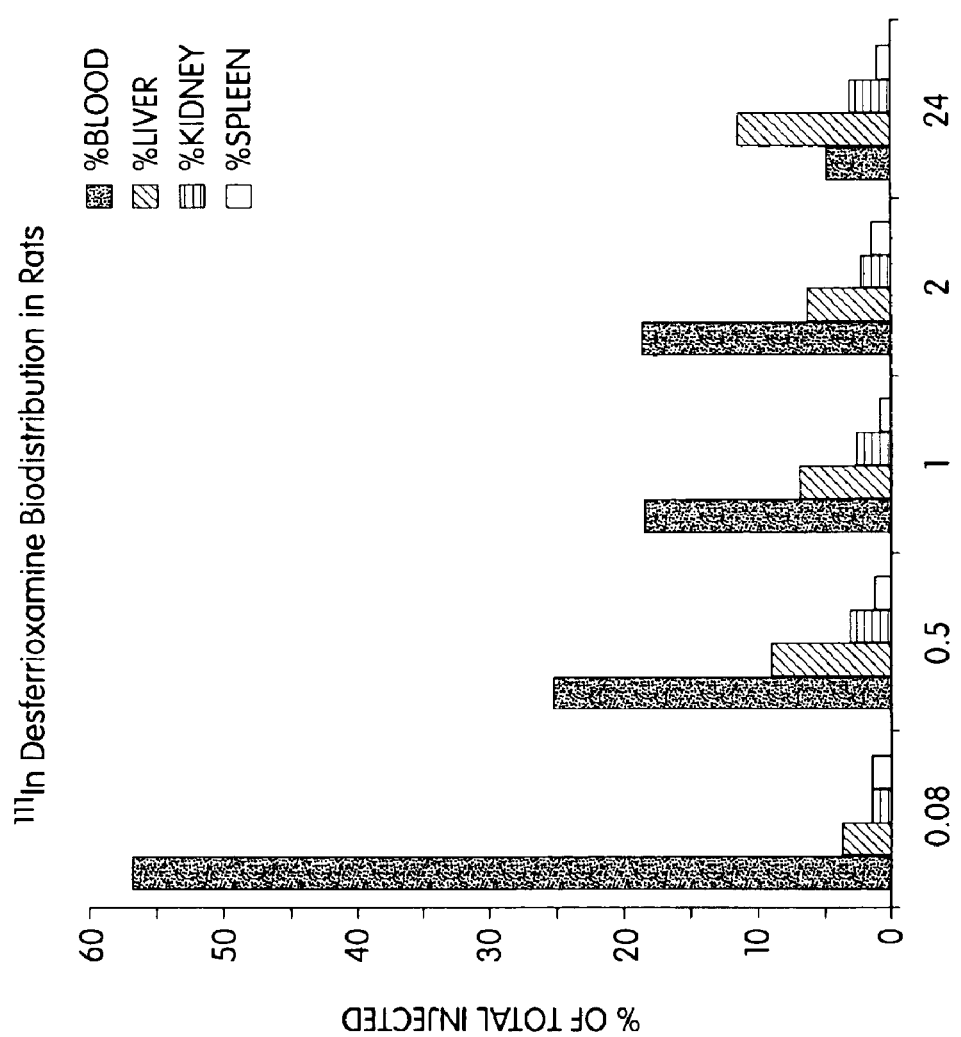
Figure 14:
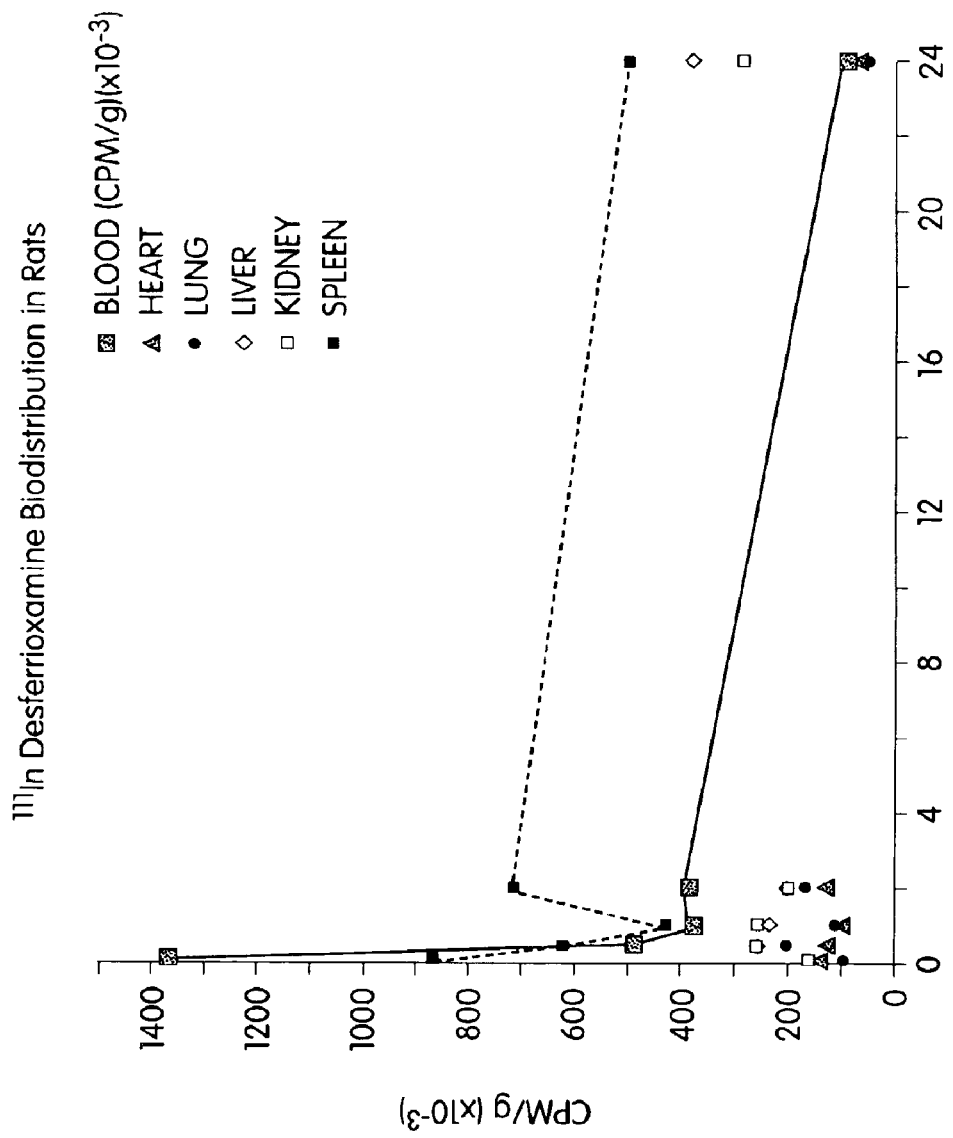
Figure 15:
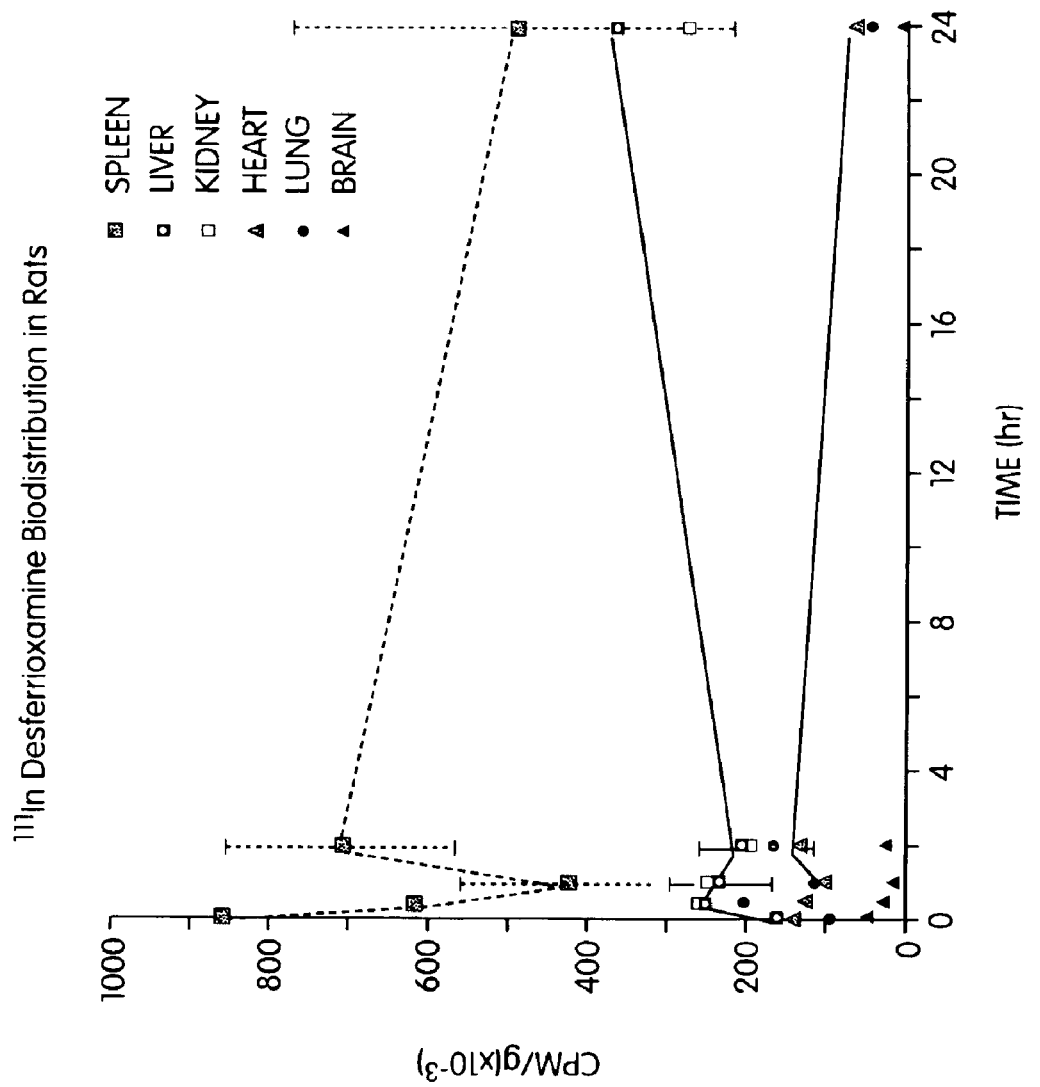
Figure 16:
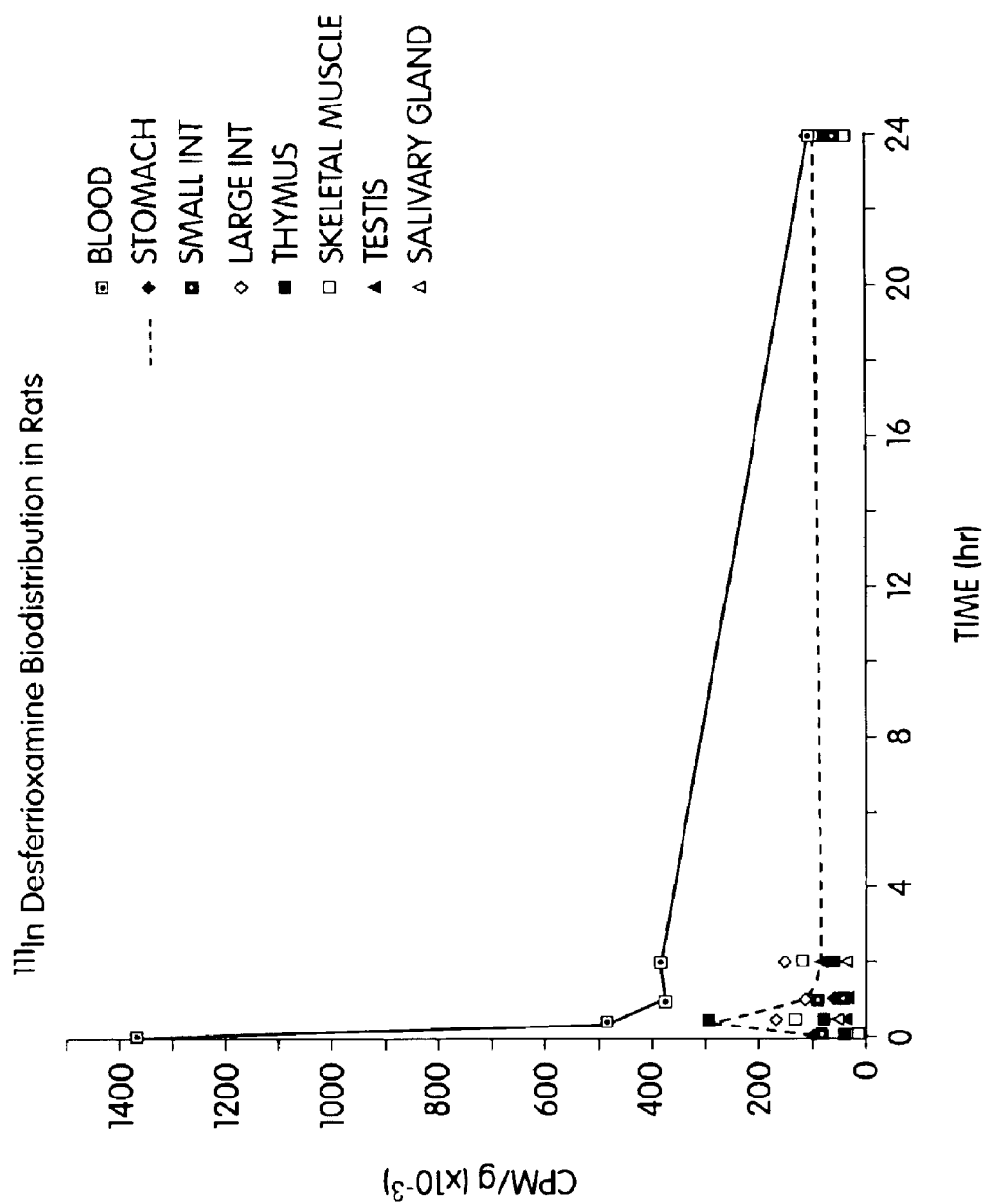
Figure 17:
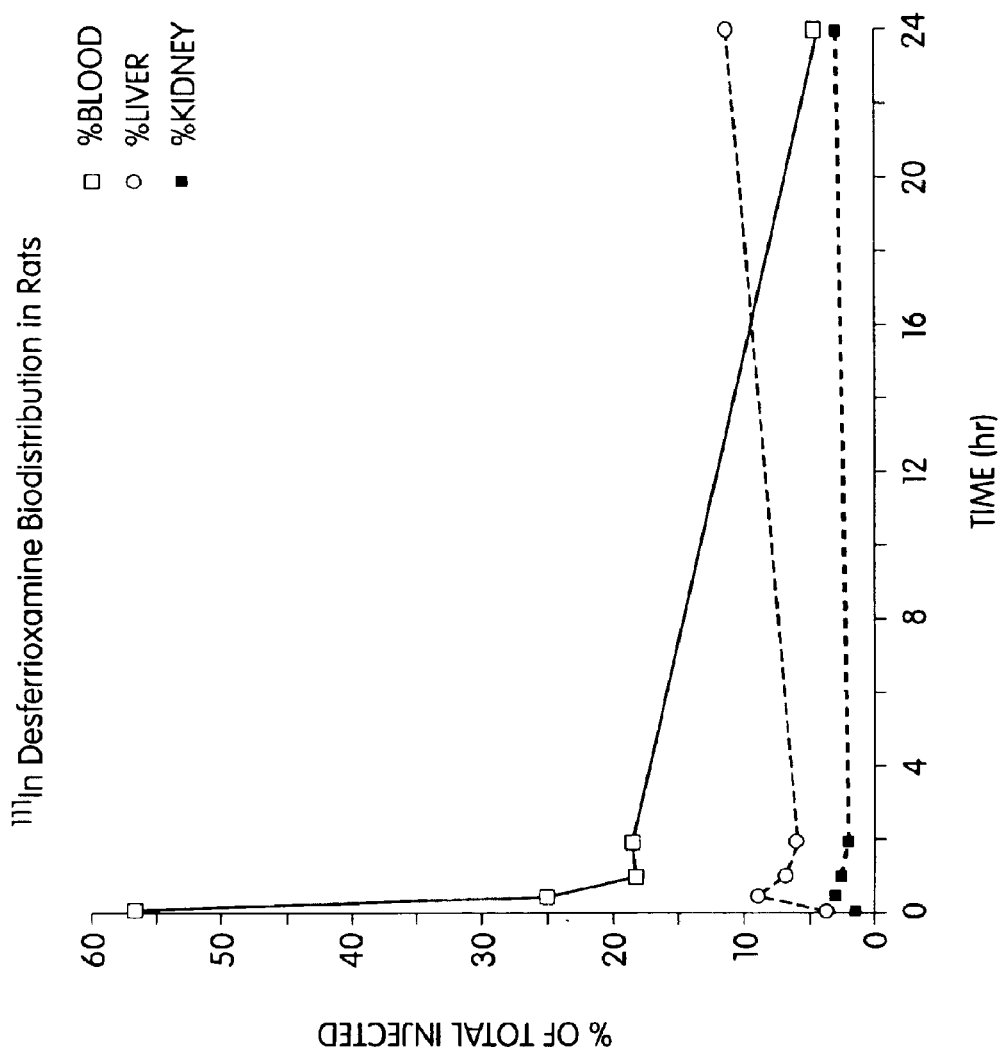
Figure 18:
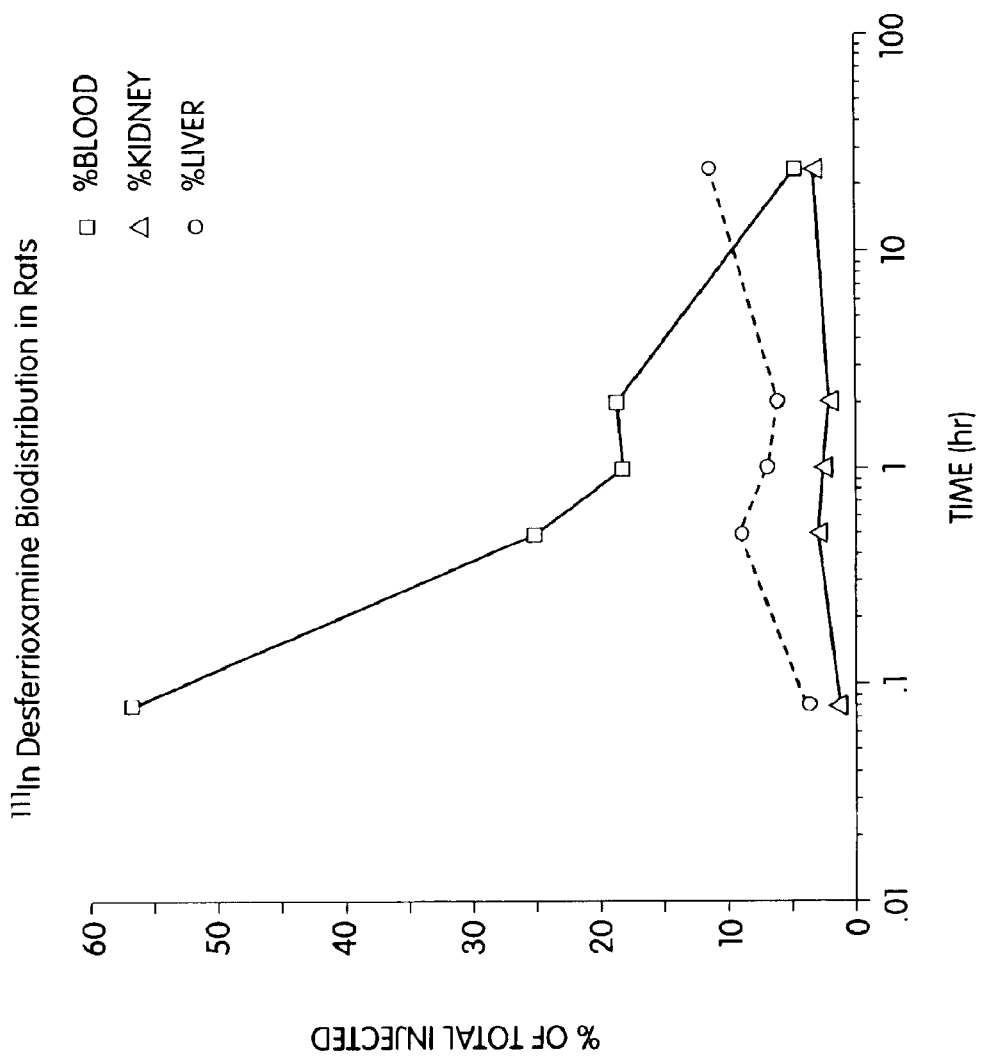

To obtain a calibration curve (FIGS. 3 and 4), 10 mg Desferrioxamine Mesylate is dissolved in 1200 ml of methanol and a stock solution generated. 0.1 ml, 0.25 ml, 0.5 ml, 0.75 ml, 1.0 ml, 1.5 ml, and 2.0 ml of this stock solution is transferred to separate volumetric flasks to form a final volume of 10 ml with the addition of methanol. Spectrophotometric absorbance for each flask is read at 204 nm.

Method 1: Liposomes are prepared by the reverse phase evaporation technique (Tabak, A. et al. (1994) J. Pharm. Pharmacol. 46:789–796). Phosphatidyl choline (PC) 0.5 mg and 4.5 mg cholesterol (Ch) are dissolved in 4 ml of chloroform ($CHCl_3$). The aqueous phase containing 12 mg Desferrioxamine Mesylate in 2 ml of saline is added to the above organic phase. The two phases are vortexed for 4 minutes for formation without emulsion. Liposomes are obtained by evaporating the organic phase under a partial vacuum produced by a water aspirator on a rotary evaporator at 20° C.–30° C. The resulting liposomes are extruded through 1.0, 0.6, 0.4, and 0.2 $\mu$m Nucleopore polycarbonate membrane filters sequentially (membrane filter pore sizes may be varied to obtain liposomes of larger sizes). The nonliposomal Desferrioxamine is removed by using the Sephadex G-50 spin-column centrifugation method. Briefly, the bottom of a 3 ml disposable syringe (0.5 cm internal diameter) is plugged with clean, silanized glass wool. A Sephadex G-50 slurry is loaded into the syringe—column. The syringe is placed into a 15 ml polypropylene tube and spun for 3 minutes at 12500 rpm in order to pack the column. A 0.25 ml sample is then loaded onto the column and centrifuged for 3 minutes at a speed of 1500 rpm. Twenty-five $\mu$l of eluant is transferred to a volumetric flask and made up to a final volume of 10 ml with methanol. The flask is then shaken to extract intraliposomal Desferrioxamine. Spectrophotometric absorbence of the solution is determined at 204 nm.

Method 2: A mixture of phosphatidyl choline (PC) and cholesterol (16 mg PC: 8 mg Ch) in $CHCl_3$ is dried under a stream of nitrogen and vacuum desiccated for 2 hours to remove any remaining traces of the solvent. The lipid is then hydrated by addition of 14 mg of Desferrioxamine in 4 ml of saline. Saline is passed through a Chelex column. The mixture is vortexed for 5 minutes. The resulting liposomes are extruded through 1.0, 0.6, 0.4, and 0.2 $\mu$M Nucleopore polycarbonate membrane filters, sequentially (membrane pore sizes may be varied to obtain liposomes of larger sizes). Liposomes are dialyzed overnight against saline at 4° C. to remove non-encapsulated Desferrioxamine. Intraliposomal Desferrioxamine is assayed by dissolving an aliquot of the suspension in an equal volume of Triton ×100, adding $FeCl_3$ in 0.1 M HCl and measuring the absorbence of the iron-Desferrioxamine complex at 428 nm (Young, S. P., et al. (1979) Brit. J. Haem. 41:357–363).

EXAMPLE 3

Preparation of Radiolabeled Liposomes with $^{111}In$

Desferrioxamine is prepared by activation of the carboxylic groups of Desferrioxamine with carbodiimide at pH 4.0 using a method similar to that described by Khaw et al. (Khaw, B. A. et al. (1991) J. Nucl. Med. 32:1742–1751). $8.33 \times 10^{-5}$ mM DTPLA in 250 µl $H_2O$ (pH adjusted to 4.0) is mixed with 14-fold molar excess of N-hydroxy sulfosuccinimide (NHSS) and 400 µg/40 µl 1-ethyl-3-(3-dimethylaminoproply) carbodiimide (EDC) is added. Another aliquot of NHSS is added. The reaction is allowed to proceed for 5 minutes at room temperature. The activated Desferrioxamine is added then directly into 1 mg of phostidylethanolamine in 0.1 M borate buffer at pH 8.3. At this pH, there is unidirectional coupling of the carboxyl group of the activated Desferrioxamine to the amino group of the phosphatidyl ethanolamine. Free Desferrioxamine is separated from Desferrioxamine-PE by lypophalization of the mixture and separation of the Desferrioxamine-PE by extraction with chloroform. Desferrioxamine will not be soluble, but Desferrioxamine-PE will be soluble. The chloroform is evaporated to obtain Desferrioxamine-PE. Aliquots of Desferrioxamine-PE is solubilized in 0.5 M citrate pH 5.0 to which 1–2 mCi of $^{111}In$ is added. The $^{111}In$-Desferrioxamine-PE is added to cholesterol and lecithin to prepare liposomes as described below.

EXAMPLE 4

Glycosylated and Mannosylated Lipid Carriers, e.g., Liposomes

Glycosylated liposomes are prepared by linking liposomes to a hydrophobic anchor N-glutaryl phosphatidyl ethanolamine (NGPE), which have been previously derivatized with the sugar residues. The carboxylic groups of NGPE are first activated by water soluble 1-ethyl-3 (3-dimethylaminopropyl) carbodiimide (EDC) to which ethylenediamine is then added to provide free amino groups. Thiolated galactose and mannose residues are then incorporated onto the amino groups of the ethylenediamine by the method of Lee et al. (Lee, Y. C. et al. (1976) Biochem. 15:3956–3963).

EXAMPLE 5

Iron Chelator and Galactosylated and Mannosylated Lipid Carriers, e.g., Liposomes N-glutaryl phosphatidyl ethanolamine (NGPE) (0.075 mg) is dissolved in 2-(N-morpholino) ethanesulfonic acid hemisodium salt (MES) buffer (0.016M octylglucoside in 50 mM MES). After addition of 0.6 mg 1-ethyl-3-(3-diemthyl amino propyl) carbodiimide (EDC) the resulting mixture is incubated at room temperature for 5 minutes. Ethylenediamine (100 µM) is then added to the activated NGPE and the solution kept at pH 5.0 by the addition of 1 N HCl solution. The reaction is allowed to proceed overnight with stirring and the solution is dialyzed against distilled water. Sugar residues are incorporated onto the amino groups of ethylenediamine-coupled NGPE by using 2-imino-2-methoxyethyl 1-thiogalactoside or 1-thio-mannoside to obtain galactosylated and mannosylated NGPE.

Liposomes are prepared by reverse phase evaporation technique (Ashwell, G. (1974) Adv. Enzymol. 41:99–128) as previously described and outlined above. The aqueous phase containing Desferrioxamine Mesylate and either galactosylated or mannosylated NGPE are added to the solubilized lipids. The two phases are vortexed for formation without emulsion. Liposomes are obtained by evaporating the organic phase under a partial vacuum produced by a water aspirator on a rotary evaporator. The resulting liposomes are extruded through Nucleopore polycarbonate membrane filters. The nonliposomal Desferrioxamine will be removed by Sephadex G-50 spin-column centrifugation method as described above.

EXAMPLE 6

Iron Chelator and Cationic Tagged Lipid Carriers, e.g., Liposomes

Positive (cationic) liposomes are prepared according to Caride and Zarel (Caride, W. et al. (1977) Science 1989:735–738). Cationic liposomes are prepared using lecithin, cholesterol and stearylamine (80:10:10 molar ratios). Incorporation of Desferrioxamine into the cationic liposomes is as previously described. Trace amounts of In-111 DTPA-PA are added to radiolabel liposomes.

EXAMPLE 7

Preparation of Fluorescein Desferrioxamine

An aliquot of 120 mg of Desferrioxamine and 233.64 mg of fluorescein isothiocyanate (FITC) are mixed in 50 ml of 0.1 M Na carvonate pH 9.5. A molar ratio of 3:1 of FITC: Desferrioxamine is used as described in Hentz et al. (1997) Anal. Chem. 69:4994–5000. The reaction mixture is wrapped in aluminum foil to avoid light exposure and allowed to react for at least 24 hours at room temperature. To separate fluorescent-Desferrioxamine from free fluorescein and free Desferrioxamine, the mixture is electrophoresed over a P-2 column (Bio-Rad) equilibrated in saline and samples are eluted in 2 ml fractions. The fluorescein-Desferrioxamine is eluted in the void volume of the column. The first peak is collected and used for preparing fluorescein-Desferrioxamine, Desferrioxamine, and rhodamine-liposomes.

EXAMPLE 8

Preparation of Rhodamine Labeled Liposomes Containing Unlabeled Desferrioxamine and Rhodamine Labeled Liposomes Containing Fluorescein Labeled Desferrioxamine An aliquot of 75 mg 1-α-phosphatidyl choline (20 mg/ml chloroform, Avanti Lipids) is added to a 50 ml round bottom flask. Forty-five mg of cholesterol (cholestin-3β-ol) is added to the solution of phosphatidyl choline. To this is added 373 µl of 2 mg/ml 1,2 dipalmitoyl-sn-glycero-3-phosphaethanolamine-N-(lissamine rhodamine β sulfonyl) (Avanti Lipids). The mixture is stirred by vortexing until thoroughly mixed. The mixture is then evaporated with a rotary evaporator set at 42° C. for 1 hour at 160 rpm. One hundred and twenty mg of Desferrioxamine is dissolved in 20 ml of physiological saline and then added to the evaporated lipids in the rotary evaporation flask. To this mixture is added 10% (vol/vol) of fluorescein-Desferrioxamine (approximately 2 ml). The mixture is stirred vigorously with a vortexed mixer. The unilamella liposomes are chromatographed using multiple columns of PD-10 (Pharmacia, Sephadex-G25) for column centrifugation as described. The liposomes that are eluted in the eluate are pooled and extruded at least 5 times each serially through 0.8, 0.45, and 0.22 micron diameter nucleopore filters. A total of 120 mg of lipids is collected in a total of 20 ml of physiological saline. Assuming a loss of 20% in the column centrifugation, the final lipid concentration in the 20 ml sample is approximately 96 mg/ml of Desferrioxamine and 9.6 mg of fluorescein-Desferrioxamine.

To prepare rhodamine liposomes with non-fluorescent Desferrioxamine, the fluorescein-Desferrioxamine is not included in the above formulation and the remainder of the protocol remains the same.

EXAMPLE 9

Targeted Delivery of Iron Chelator System

Targeted delivery of iron chelator delivery systems comprising, for example, Desferrioxamine and liposomes, can be shown by comparing the delivery of the liposomes in normal animals with the delivery of the liposomes in animals with iron-overload. Radiolabeled liposomes can be used to quantify the localization into targeted tissues and, for example, the effect on heart function in particular arrhythmogenesis and contractile dysfunction can be evaluated.

The Heart: Iron chelator delivery systems comprising, for example, Desferrioxamine and liposomes, for targeting the heart include placing a cationic or anionic charge groups on the liposomes which might adversely affect the conduction system of the heart. Injection of the Desferrioxamine and liposome system can be done intra-venously. Caride and Zaret in 1977 (Caride, W. J. (1977) Science 1989:735–738) showed that positively charged liposomes can be targeted specifically for acute myocardial ischemia or infarction in an experimental model. When uptake was compared to regional myocardial blood flow, it was observed to have an inverse correlation to the liposome distribution. Negatively charged (anionic) liposomes, however, distributed relative to blood flow. Since there is a myocardial blood flow, it was observed to have an inverse correlation to the liposome distribution. Since there is myocardial involvement in iron toxicity, there is possibility of damage to the myocardium. Therefore, cationic or anionic liposomes will also localize preferentially in iron-overloaded myocardium. Another approach would be to tag the iron chelator delivery system with antibodies targeted to cardiac specific endothelial cells, vascular smooth muscle cells, matrix proteins, receptors, and/or myocardial cells.

The Liver: Carbohydrate receptors in the liver, such as asialoglycoprotein receptors on the hepatocytes and mannose receptors on Kupfer cells and endothelial cells, allow selective targeting of this organ (Ashwell, G. (1974) Adv. Enzymol. 41:99–128), (Ashwell, G. (1982) Ann. Rev. Biochem. 51:531–554), (Fallon, R. J. (1989) Adv. Drug Del. Rev. 4:49–63), (Gordon, S. (1989) Adv. Drug Del. Rev. 4:27–47), (Meijer, D. K. F. (1989) Phar. Res. 6:105–118) by the Desferrioxamine-encapsulated liposomes. Liposomes can be utilized as carrier molecules because of their low immunogenicity, their relative biocompatability, and their drug encapsulation efficiency. With glycosylated liposomes the targeting efficiency to the liver is increased.

EXAMPLE 10

Determination of the Toxicity of the Iron Chelator Delivery System

Toxicity in the administration of the iron chelator delivery system, e.g., Desferrioxamine combined with a lipid carrier, e.g., a liposome, can be tested in animal models. For example, two species of normal animals and iron-overloaded animals (e.g., the guinea pig) can be compared. One group of animals receives the delivery system comprising Desferrioxamine and a lipid carrier, e.g., Desferrioxamine-encapsulated within a liposome, and another group receives similar liposomes without the Desferrioxamine. Animals are monitored for cardiac arrhythmias via electrocardiogram once a week. Heart function is determined with echocardiography at the same time that electrocardiograph recordings are made at one and at 24 hour intervals post-injection followed by weekly monitoring for up to 6 weeks. Full necropsy is performed with special attention to harvesting the liver and heart. In humans, the infusion of the iron chelator delivery system, e.g., Desferrioxamine combined with a lipid carrier, e.g., Desferrioxamine encapsulated within a liposome, would take between 20 minutes and one hour. Repeat treatments typically would occur over a 3–6 week interval. Therefore cardiac and liver functions are monitored in the animals after one hour, 24 hours, and at weekly intervals up to ten weeks.

Local skin irritation at the infusion site is a complaint of the current formulation of Desferrioxamine. Irritation should not occur with the use of the present iron chelator delivery system, e.g., Desferrioxamine encapsulated within a liposome, because liposomes are given intravenously. Animal body weight, serial hematocrits, blood iron levels, and ferritin plasma levels are determined on individual animals. Blood samples are analyzed with full differential including creatinine and complete CBC to check for agranulocytosis as seen with Deferipone. Analysis of liver enzymes including SGOT, SGPT, alkaline phosphatase, BUN, is performed once a week. Urine excretion or iron is measured in iron-overload animals by atomic absorption spectroscopy.

Dosing range, safety, and toxicity studies in normal animals, as well as, quantification of any toxicity seen in the liver, heart, gastrointestinal tract, kidney, and at the injection site is important. At the time of full body necropsy tissue weights and gross appearance is recorded. The heart and liver are stored in 10% phosphate buffered formalin. Other body organs are also stored in 10% buffered formalin for future light miscroscopy, or special staining. Prussian blue iron stain is applied to liver and heart samples. Quantitative analysis using a point counting technique and semiquantitative technique using a scale of ±4 can be used. All measurements should be made by a single observer.

Flame photometry atomic absorption spectroscopy measurements are carried out on fresh or lyophilized liver and heart with either normal iron depot or iron-overload with or without the present iron chelator delivery system, e.g., Desferrioxamine encapsulated within a liposome, administered. Normal animals treated with Applicants' iron chelator delivery system, e.g., Desferrioxamine encapsulated within a liposome, and non-treated normal animals are compared for possible reduction in normal iron levels. Iron deficiency can in itself result in cardiomyopathy. Similar studies would be applied to Mongolian gerbils and rats with iron-overload and thalassemic rats.

EXAMPLE 11

Determination and Comparison of the Biological Half-life of Iron Chelator Delivery Systems Iron-overloaded rats are given iron chelator delivery systems comprising, for example, Desferrioxamine and liposomes. Iron blood levels are measured before and after injection. Pharmacokinetic studies are performed in both iron-overloaded and normal animals with radiolabeled liposomes. One group of animals also receives the standard formulation of Desferrioxamine injected over a 24 hour period via a minipump similar to the standard procedure for humans receiving the compound. The localization of Desferrioxamine will be radiolabeled for imaging and quantification of organ localization.

Imaging: Male and female rats age 10–12 weeks are injected intravenously with 100 $\mu$Ci $^{111}$In-Desferrioxamine liposomes (4 $\mu$Ci/$\mu$mol lipid, fluid liposome type) or 100 $\mu$Ci free $^{111}$In-Desferrioxamine. The amount of Desferrioxamine to be injected is determined in experiments without radiolabeling using fluorescent labels. Rats are anesthetized (halothane-nitrous oxide-oxygen) and placed prone on a single head camera equipped with a parallel hole, medium energy collimator to image the entire body with special focus on liver, kidney, brain, and heart. Symmetric 20 percent windows are focused for both 173 and 247 KeV energy peaks. Images (100,000 counts/image) are obtained and stored in a 256×256 matrix. The scintigraphic results are analyzed by drawing regions of interest. Images are obtained at 0.5, 1, 2, 4, 6, 24, 48, 72, 96, and 144 hours after injection of $^{111}$In-Desferrioxamine-liposomes and free drug (five rats per time point).

The amount of liposome-entrapped Desferrioxamine was found to be highest in the liver and had a longer biological half-life than the iron chelator alone (FIGS. 6–18).

Pharmacokinetics/Biological Half-Life Determinations: Pharmacokinetic studies are performed in both iron overloaded and normal animals with radiolabeled liposomes. Pharmacokinetic parameters are calculated using the curve fitting program KINFIT. Values of $^{111}$In-Desferrioxamine in blood versus time are fitted by a model for extravesicular administration and two compartments without lag time. The half-life of blood levels of liposome-entrapped Desferrioxamine is determined.

EXAMPLE 12

Toxicity Study in Normal Animals

Safety studies were performed in six 200 gram female rats. Three rats were injected via tail vein with 2 ml of iron chelator delivery systems comprising, for example, Desferrioxamine and liposomes, (10 mg). Three additional animals received the liposomes without Desferrioxamine. No toxicity or morbidity was noted up to ten days post-injection. There was no irritation noted at the injection site.

Blood Chemistry Values Before and After Liposome Infusion (with and without Desferrioxamine) were not significantly different (FIG. 5).

Rats were anesthetized and allowed to breathe spontaneously during fluid filled catheter recordings of LV pressure. Closed chest LV systolic pressures were 180±4 mm Hg before intravenous injection of the Desferrioxamine-encapsulated liposomes versus 181±4 after injection. At one hour after injection the LV systolic pressure was 175±5 mm Hg (p>0.05).

Simple semiquantitative analysis of tissues from animals receiving the liposomes without Desferrioxamine and liposomes with Desferrioxamine (i.e., liver and heart) stained for iron revealed no differences by light microscopic examination.

EXAMPLE 13

Histological Findings of Rats Injected with Rhodamine Labeled Liposomes Containing Fluorescein Labeled Desferrioxamine Forty-two rats were injected with 2 cc of rhodamine labeled liposomes containing 0.6 mg/ml of Desferrioxamine labeled with fluorescein. Heart, liver, brain, and both kidneys were harvested. Tissues were frozen for later fluorescent imaging or stored in buffered formalin, sectioned, and stained with hematoxylin and eosin and counter stained with Masson's trichrome. Histological reading by a board certified laboratory veterinary pathologist reported no remarkable change. No morbidity or toxicity was noted up to ten days post-injection. There was no irritation noted at the injection site. An additional group of animals were euthanized at 30 minutes, 1 hour, and 24 hours post-injection of Desferrioxamine labeled with fluorescein entrapped in liposomes labeled with rhodamine. Histological analysis showed fluorescent labeling in the liver of liposomes and of Desferrioxamine in the Kupffer cells at the 30 minute time point. Discrete localization was seen up to two hours post-injection. The 24 hour time point demonstrated homogenous fluorescence due to re-distribution of the lipids in the liposomes and Desferrioxamine. There was no detected organ damage. No signs of toxicity were noted in any of the experiments at the organ level or clinical presentation. The brain was examined for histological changes as lipids can easily cross the blood brain barrier. No indication was found of liposome distribution in the brain, heart, or kidney.

EXAMPLE 14

Biodistribution of the Iron Chelator Delivery System

Rats are injected intravenously with 10 $\mu$Ci $^{111}$In-Desferrioxamine liposomes or 10 $\mu$Ci free $^{111}$In-Desferrioxamine at a total dose of 25 $\mu$mol Desferrioxamine targeted (injection volume 0.5 ml). At predefined time points after injection, rats receive an overdose of pentobarbitol and blood is obtained by cardiac puncture. The following tissues are dissected: injection site; muscle; lung; spleen; kidney; liver; heart; and brain. These tissues are also weighed and the activity measured in a shielded well-type gamma counter. To correct for physical decay and to calculate uptake in each organ as a fraction of the injected dose, aliquots of the injected dose are counted simultaneously.

With reference to FIGS. 6–18, following the injection of radiolabeled Desferrioxamine, radioactivity is observed in the kidney and the spleen. Lung, spleen, blood, skeletal muscle, brain, heart, and liver are also radioactive. No radioactivity is observed in the brain, indicating that the iron chelator delivery system does not cross the blood brain barrier. As the radioactivity in the blood drops over time, the liver localization of the radioactive iron chelator delivery system in the liver increases. Subsequently, the chelated Desferrioxamine is removed from the liver.

Radiolabeled chelator without liposomes was quickly eliminated from the animals and did not accumulate in the tissues, especially the liver and tracked blood distribution.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. An iron chelator delivery system for treating iron overload in the liver, comprising an iron chelator and a lipid carrier, wherein said lipid carrier further comprises a liver cell targeting agent for targeting at least one liver carbohydrate receptor and wherein the concentration of the iron chelator is about 1 $\mu$M to about 100 mM.

2. The iron chelator system of claim 1, wherein the liver cell targeting agent is selected from the group consisting of asialoglycoprotein, galactose and mannose.

3. The iron chelator delivery system of claim 1, wherein the liver carbohydrate receptor is selected from the group consisting of a hepatocyte asialoglycoprotein receptor, a Kupffer cell mannose receptor, and a liver endothelial cell mannose receptor.

4. The iron chelator delivery system of claim 1, wherein the iron chelator is selected from the group consisting of Desferrioxamine, deferipone, PIH, Rhodotorulic acid, HBED, HBPD, 2,3-dihydroxybenzoic acid, DTPA and iron chelators produced by bacterial siderophores.

5. The iron chelator delivery system of claim 1, wherein the lipid carrier is a liposome.

6. The iron chelator delivery system of claim 1, wherein the liver carbohydrate receptor is a Kupffer cell mannose receptor.

7. The iron chelator delivery system of claim 1, wherein the iron chelator is in the lipid carrier.

* * * * *